US006623470B2

(12) United States Patent
Munis et al.

(10) Patent No.: US 6,623,470 B2
(45) Date of Patent: Sep. 23, 2003

(54) METHOD AND APPARATUS FOR CONTROLLING BLOOD VOLUME AND HYDRATION AND FOR INDICATING RESUSCITATION STATUS OF A PATIENT USING PERIPHERAL VENOUS PRESSURE AS A HEMODYNAMIC PARAMETER

(75) Inventors: James Robert Munis, Novelty, OH (US); Leonardo Jose Lozada, Shaker Heights, OH (US); Andrew Michael Zura, Broadview Heights, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/892,820

(22) Filed: Jun. 27, 2001

(65) Prior Publication Data

US 2003/0004492 A1 Jan. 2, 2003

(51) Int. Cl.⁷ .............................. A61M 31/00; A61B 5/02
(52) U.S. Cl. .................... 604/503; 604/500; 604/66; 604/65; 604/67; 600/485; 600/486
(58) Field of Search ................ 604/503, 65, 66, 604/67, 131, 500, 50, 246, 247, 118; 600/486, 485

(56) References Cited

U.S. PATENT DOCUMENTS

| 3,693,612 | A | * | 9/1972 | Donahoe et al. ............ 128/2.05 |
|---|---|---|---|---|
| 3,980,082 | A | * | 9/1976 | Miller .................... 128/214 R |
| 4,297,890 | A | * | 11/1981 | Hok ............................. 73/753 |
| 4,300,572 | A | * | 11/1981 | Knighton .................... 128/674 |
| 4,342,218 | A | * | 8/1982 | Fox ............................. 73/4 R |
| 4,601,706 | A | * | 7/1986 | Aillon ......................... 604/53 |
| 4,648,406 | A | * | 3/1987 | Miller ........................ 128/674 |
| 4,657,490 | A |   | 4/1987 | Abbott |
| 4,739,769 | A | * | 4/1988 | Matthews et al. .......... 128/673 |
| 4,857,048 | A |   | 8/1989 | Simons et al. |
| 4,947,856 | A | * | 8/1990 | Beard ......................... 128/673 |
| 4,979,940 | A | * | 12/1990 | Bobo, Jr. et al. ............. 604/50 |
| 4,986,277 | A |   | 1/1991 | Sackner |
| 5,116,312 | A |   | 5/1992 | Blankenship et al. |
| 5,280,789 | A | * | 1/1994 | Potts .......................... 128/673 |
| 5,302,093 | A |   | 4/1994 | Owens et al. |
| 5,423,323 | A | * | 6/1995 | Orth ........................... 128/673 |
| 5,429,485 | A |   | 7/1995 | Dodge |
| 5,437,635 | A |   | 8/1995 | Fields et al. |
| 5,769,083 | A | * | 6/1998 | MacEachern ............... 128/673 |
| 5,772,634 | A | * | 6/1998 | Atkinson .................... 604/118 |
| 5,840,068 | A |   | 11/1998 | Cartledge |
| 6,302,864 | B1 | * | 10/2001 | Nowosielski ................. 604/65 |
| 6,371,937 | B1 | * | 4/2002 | McPhee ..................... 604/118 |

OTHER PUBLICATIONS

An article entitled "Peripheral Venous Pressure as a Hemodynamic Variable in Neurosurgical Patients" by Munis et al., Anesth. Analg. 92:172–9, 2001.

(List continued on next page.)

Primary Examiner—Ira S. Lazarus
Assistant Examiner—Tu Cam Nguyen
(74) Attorney, Agent, or Firm—Tarolli, Sundheim, Covell & Tummino L.L.P.

(57) ABSTRACT

An apparatus for controlling fluid volume in a patient includes a fluid source (16) and a fluid conduit (32, 34, 36) for carrying fluid from the fluid source to the patient (12). A controllable infusion pump (30) pumps fluid from the fluid source to a peripheral vein of the patient through the fluid conduit. An occluder (100) for blocks fluid communication between the fluid source and the patient through the fluid conduit. A fluid pressure sensor (80) periodically senses fluid pressure in the fluid conduit. The apparatus further includes a controller (86) for determining a peripheral venous pressure value from the sensed fluid pressure in the fluid conduit after the infusion pump is stopped and the occluder blocks the fluid communication between the fluid source and the patient through the fluid conduit. The peripheral venous pressure is indicative of the patient's means systemic pressure and the fluid volume of the patient.

42 Claims, 4 Drawing Sheets

OTHER PUBLICATIONS

An article entitled "Correlation of Peripheral Venous Pressure and Central Venous Pressure in Surgical Patients" by Amar et al., Journal of Cardiothoracic and Vascular Anesthesia, vol. 15, No. 1 (Feb.): pp. 40–43., 2001.

An article entitled "The Effect of Positive and Negative Intra–Thoracic Pressure on Peripheral Venous Pressure in Man" by Holt, Am. J. Physiol.; 139:208–211, 1943.

An article entitled "The Pressure in the Central Veins and Its Bearing on Peripheral Venous Pressure Measurement" by Pedersen, Aacta med. scand., 142, Suppl. 266:829–837, 1952.

An article entitled "A Comparison Between Peripheral and Central Venous Pressure Monitoring Under Clinical Conditions" by Eustace, Injury: The British Journal of Accident Surgery, vol. 2, No. 1 (Jul.): pp. 14–18, 1970.

An article entitled "Peripheral Postcapillary Venous Pressure—A New Hemodynamic Monitoring Parameter" by Sheldon et al., Surgery, vol. 92, No. 4 (Oct.): pp. 663–669 1982.

An article entitled "Peripheral Postcapillary Venous Pressure: A New, More Sensitive Monitor of Effective Blood Volume During Hemorrhagic Shock and Resuscitation" by Sheldon et al., Surgery, vol. 94, No. 2 (Aug.): pp. 399–406, 1983.

An article entitled "Cuff–Occluded Rate of Rise of Peripheral Venous Pressure: A New, Highly Sensitive Technique for Monitoring Blood Volume Status During Hemorrhage and Resuscitation" by Wolf et al., Surgery, vol. 101, No. 3 (Mar.): pp. 304–309, 1987.

An article entitled "Peripheral Venous Monitoring With Acute Blood Volume Alteration: Cuff–Occluded Rate of Rise of Peripheral Venous Pressure" by Snyder et al., Critical Care Medicine, vol. 18, No. 10 (Oct.): pp. 1142–1145, 1990.

An editorial entitled "Giraffes, Siphons, and Starling Resistors—Cerebral Perfusion Pressure Revisited" by Munis et al., Journal of Neurosurgical Anesthesiology, vol. 12, No. 3 (Jul.): pp. 290–296, 2000.

An abstract entitled "Peripheral Venous Pressure Predicts Intraoperative Central Venous Pressure" by Amar et al., Anesthesiology, vol. 89, No. 3A (Sep.): Abstract No. A946, 1998.

An abstract entitled "Peripheral Venous Pressure Predicts Central Venous Pressure in the Post–Anesthesia Care Unit" by Amar et al., Anesthesiology, vol. 91, No. 3A (Sep.): Abstract No. A545, 1999.

* cited by examiner

METHOD AND APPARATUS FOR CONTROLLING BLOOD VOLUME AND HYDRATION AND FOR INDICATING RESUSCITATION STATUS OF A PATIENT USING PERIPHERAL VENOUS PRESSURE AS A HEMODYNAMIC PARAMETER

TECHNICAL FIELD

The present invention is directed to a method and apparatus for controlling blood volume and hydration, and for indicating resuscitation status of a patient using peripheral venous pressure as a hemodynamic parameter.

BACKGROUND OF THE INVENTION

Patients undergoing major surgery are at risk for significant blood loss and hemodynamic changes while under anesthesia. A portion of that risk is associated with the surgery itself, and the remainder is attributable of the effects of anesthetics, mechanical ventilation, positional changes on cardiac function, relative blood volume, and vascular tone. Oxygen carrying capacity as well as the body's efficiency in removing carbon dioxide and metabolic wastes are a function of blood volume.

For patients having procedures with a likelihood of significant blood loss, or for patients in whom hemodynamic changes are especially threatening because of coincident cardiovascular disease, central venous pressure ("CVP") monitoring has been widely used. CVP is a direct measure of blood pressure, not blood volume. In a normal range of hemodynamic values, CVP appears to have more utility as a trend monitor than for titration to an absolute end point.

The measurement of CVP requires the insertion and maintenance of a catheter in the thorax. Typically, the catheter is positioned in the superior vena cava from an insertion site in an external or internal jugular vein, subclavian vein, or, less often, from a femoral or antecubital vein. CVP placement adds time and monetary costs to surgery. Also, CVP measurements typically include respiratory variations and cardiac excursions that must be considered during monitoring.

The need to control blood volume and hydration and assess resuscitation status are particularly important in neurosurgical patients undergoing either craniotomy or complex spine surgery. It is also important to control hydration in hospitalized patients as well as nursing home patients.

SUMMARY OF THE INVENTION

In accordance with the present invention, control of blood volume and hydration, and indicating resuscitation status of a patient is achieved using peripheral venous pressure as a hemodynamic parameter. The present invention is useful for patients undergoing surgery or trauma patients as well as hospitalized patients and nursing home patients.

In accordance with one aspect of the present invention, an apparatus for measuring peripheral venous pressure in a patient comprises a fluid source and a fluid conduit for carrying fluid from the fluid source to the patient. A pump pumps fluid from the fluid source to the patient through the fluid conduit. The apparatus further includes means for measuring fluid pressure in the fluid conduit indicative of the peripheral venous pressure of the patient.

In accordance with another aspect of the present invention, an apparatus comprises a fluid source, a pump for pumping fluid from the fluid source to a patient, means for measuring a value functionally related to mean systemic pressure of the patient, and means for controlling the pump in response to the measured value functionally related to the mean systemic pressure of the patient.

In accordance with another aspect of the present invention, an apparatus comprises a fluid source, a pump for pumping fluid from the fluid source to a patient, means for measuring peripheral venous pressure of the patient, and means for controlling the pump in response to the measured peripheral venous pressure of the patient.

In accordance with still another aspect of the present invention, an apparatus for controlling fluid volume in a patient comprises a fluid source and a fluid conduit for carrying fluid from the fluid source to the patient. A controllable infusion pump pumps fluid from the fluid source to a peripheral vein of the patient through the fluid conduit. An occluder blocks fluid communication through the fluid conduit between the fluid source and the patient. A fluid pressure sensor senses fluid pressure in the fluid conduit. The apparatus further includes a controller for determining a peripheral venous pressure value from the sensed fluid pressure in the fluid conduit after the infusion pump is stopped and the occluder blocks the fluid communication through the fluid conduit between the fluid source and the patient. The peripheral venous pressure is indicative of fluid volume of the patient.

In accordance with still another aspect of the present invention, an apparatus for controlling fluid volume in a patient comprises a fluid source and a controllable infusion pump connected to the fluid source through a fluid inlet line. The apparatus includes a catheter inserted in a peripheral vein of a patient and connected from an outlet of the infusion pump through a fluid outlet line so as to provide a fluid communication path between the peripheral vein of the patient and the pump. Activation of the pump results in fluid being delivered to the patient from the fluid source through the catheter. An in-line pressure sensor is positioned substantially at a heart level of the patient for sensing pressure in the fluid communication path and providing a pressure measurement signal indicative thereof. The apparatus further includes an actuatable in-line occluder for isolating the fluid source from the patient when the occluder is actuated and control means for periodically stopping the infusion pump, actuating the occluder, monitoring the pressure measurement signal, and determining a peripheral venous pressure value of the patient in response thereto. Means are provided for adjusting operation of the infusion pump in response to the determined peripheral venous pressure value.

In accordance with another aspect of the present invention, a method for measuring peripheral venous pressure in a patient comprises the steps of connecting a fluid source to the patient through a fluid conduit, pumping fluid from the fluid source to the patient through the fluid conduit, and measuring fluid pressure in the fluid conduit indicative of the peripheral venous pressure of the patient.

In accordance with another aspect of the present invention a method comprises the steps of pumping fluid from a fluid source to a patient, measuring a value functionally related to mean systemic pressure of the patient, and controlling the pumping in response to the measured value functionally related to mean systemic pressure of the patient.

In accordance with another aspect of the present invention, a method comprises the steps of pumping fluid from a fluid source to a patient, measuring peripheral venous pressure of the patient, and controlling the pumping in response to the measured peripheral venous pressure of the patient.

In accordance with yet another aspect of the present invention, a method for controlling fluid volume in a patient comprises the steps of connecting a fluid source to the patient through a fluid conduit, periodically pumping fluid with an infusion pump from the fluid source to a vein of the patient through the fluid conduit, periodically occluding fluid communication through the fluid conduit between the fluid source and the patient, periodically sensing fluid pressure in the fluid conduit, monitoring the sensed fluid pressure in the fluid conduit after (i) pumping stops, and (ii) occluding blocks the fluid communication through the fluid conduit between the fluid source and the patient, and providing an indication of the monitored fluid pressure, the monitored fluid pressure being indicative of fluid volume of the patient.

BRIEF DESCRIPTION OF THE DRAWINGS

The foregoing and other features and advantages of the present invention will become apparent to those skilled in the art to which the present invention relates upon reading the following description with reference to the accompanying drawings, in which.

DESCRIPTION OF PREFERRED EMBODIMENT

It is desirable to control the ratio of blood volume to total vascular compliance in a patient and in particular, the ratio of the stressed blood volume to vascular compliance. The stressed blood volume is the amount of blood volume above the unstressed or priming blood volume. The unstressed blood volume is that amount of blood necessary to begin to stretch the vessel walls of the cardiovascular system so that pressure begins to rise above zero. Below this unstressed blood volume value, the heart pumps empty and is no longer able to generate a cardiac output or maintain an elevated arterial blood pressure. Once blood volume rises above the unstressed volume of the cardiovascular system, the venous pressure begins to rise as a function of the compliance curve of the blood vessels.

The ratio of stressed blood volume to vascular compliance is the mean systemic pressure ("$P_{ms}$"). $P_{ms}$ is the effective upstream pressure that drives venous return and, ultimately, cardiac output. It has been discovered by applicants that $P_{ms}$ is also the pressure that the cardiovascular system converges to during circulatory arrest and is useful in estimating a patient's blood volume, hydration, and resuscitation status.

It has been discovered by applicants that peripheral venous pressure ("PVP") is indicative of $P_{ms}$. In effect, applicants have discovered that PVP is indicative of the patient's mean systemic pressure, the pressure to which all vascular beds converge in the absence of cardiac function. PVP is indicative of the ratio of blood volume to vascular compliance and is, therefore, a useful hemodynamic parameter for measuring blood volume and hydration, and for indicating resuscitation status.

For the purposes of description herein, pressure is measured in and described in terms of millimeters mercury ("mmHg"). Flow rates are measured in and described in terms of cc/hr. Applicants have discovered that, although there is a pressure differential between CVP and PVP (PVP being greater than CVP), correlation between CVP and PVP is substantially linear over a wide range of pressure. PVP reflects an upstream venous variable and is coupled to CVP by a continuous column of blood. The differential between the two is variable from patient to patient. However, in an individual patient, the difference between PVP and CVP is substantially constant. In studies conducted by the applicants, the correlation between PVP and CVP is approximately 0.997. CVP measurements, however, include respiratory variations and cardiac excursions.

Figure 1:
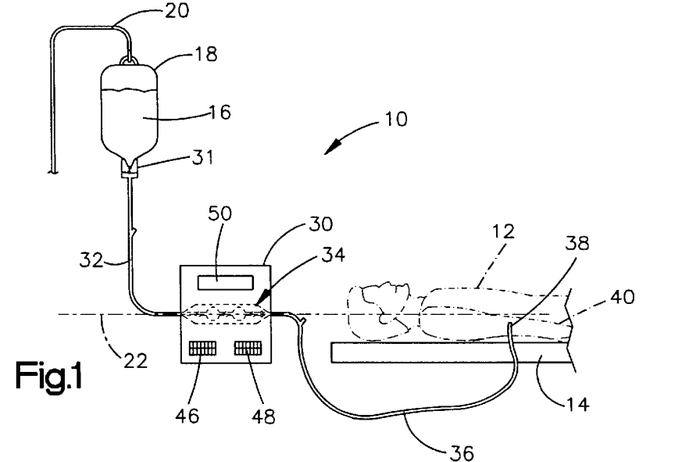
FIG. 1 is a schematic diagram of an apparatus, in accordance with the present invention, for controlling fluid volume and hydration and for indicating resuscitation status of a patient.

Referring to FIG. 1, a system 10, in accordance with the present invention, controls blood volume and hydration and indicates resuscitation status in a patient 12. The patient 12 is supported in a supine position on a support surface 14 such as an operating table during surgery or a bed during convalescence. The patient could be in a lateral or prone position. Although the present invention is described for a surgical patient, the invention is applicable to trauma patients as well as hospitalized and nursing home patients.

A gravity feed intravenous fluid source 16 such as blood, saline solution, or other desired fluids and medications in an IV bag 18 of known volume is supported on a stand 20 and positioned well above a heart level 22 of the supined patient 12. The fluid source 16 is in fluid communication with an infusion pump 30 through a transparent drip chamber 31 and fluid inlet line 32 and a disposable cassette 34. The disposable cassette 34 is, in turn, in fluid communication with the patient 12 through an outlet fluid line 36 and a catheter 38. The catheter 38, such as an angiocatheter or any other intravascular catheter, is inserted into a peripheral vein of the patient 12 such as in the patient's arm 40. Inlet line 32, cassette 34, and outlet line 36 form a fluid conduit between the fluid source 16 and the patient 12.

The infusion pump 30 includes a data input source 46 that permits the inputting of data to the infusion pump 30 for control of the pump. The infusion pump 30 further includes manual control switches 48 for manually controlling the pump's operation. A data display 50 is provided for displaying data such as peripheral venous pressure of the patient 12, total fluid volume infused into the patient, fluid remaining in the present IV 18, fluid flow rate, etc.

Figure 2:
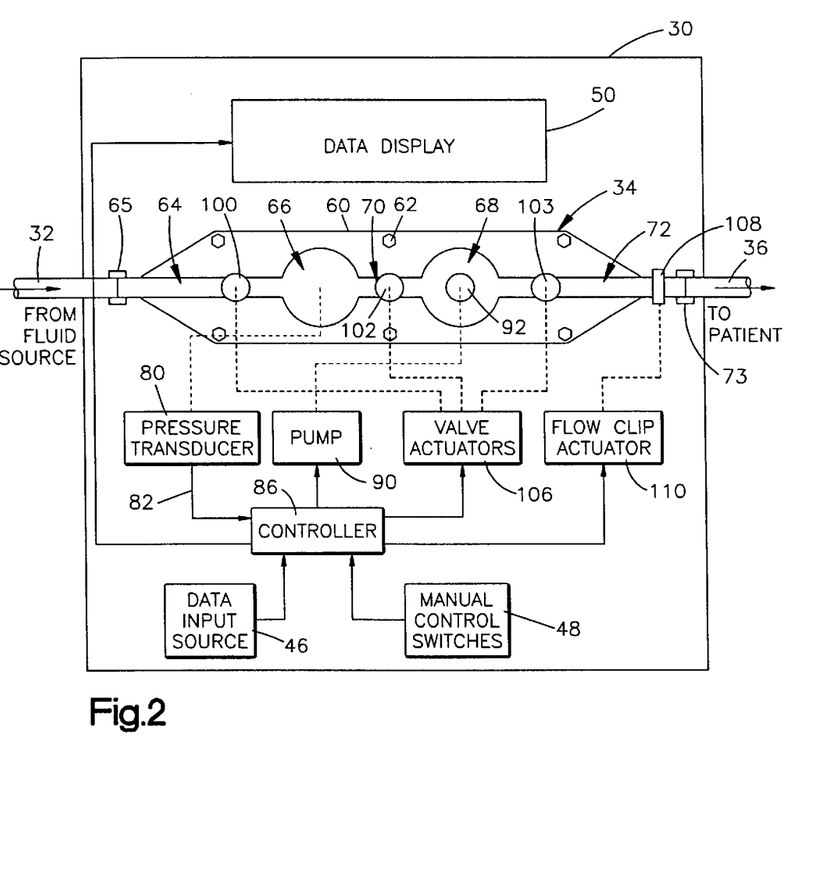
FIG. 2 is a schematic block diagram of the infusion pump of FIG. 1.

Referring to FIG. 2, the disposable cassette 34 includes a substantially flat frame portion 60 made of vinyl plastic material having mounting holes 62 arranged to be snapped into or positioned on mounting pins in the infusion pump 30 typically through a door (not shown) arrangement known in the art. The cassette 34 includes a flexible inlet passage 64 connected to the fluid inlet line 32 using a coupling 65. The inlet passage 64 is in fluid communication with a pressure sensing chamber 66 of the cassette 34 having flexible side walls that expand and contract in response to fluid pressure within the chamber 66. Fluid pressure sensing chamber 66 is in fluid communication with a fluid pumping chamber 68 of cassette 34 through a flexible fluid passage 70. The walls of the pumping chamber 68 are flexible and can be expanded or contracted via mechanical means to draw fluid into the cassette 34 and pump fluid from the cassette. The pumping chamber 68 is in fluid communication with the fluid outlet line 36 via a flexible passage 72. The coupling 73 connects passage 72 with the outlet line 36.

When the cassette 34 is operatively positioned within the infusion pump 30 with the infusion pump door (not shown) closed, the fluid pressure sensing chamber 66 is in communication with a pressure sensing transducer 80. The pressure sensing transducer 80 senses the fluid pressure within the chamber 66 and provides an electrical signal 82 to a controller 86 indicative of the pressure within the chamber 66. The pressure transducer signal 82 is indicative of fluid pressure in mmHg. The transducer 80 is used for PVP measurement and has a sensing range of 0–30 mmHg.

The pumping chamber 68 is in operative communication with a pump 90 which takes the form, in accordance with one embodiment of the present invention, of an electrically actuatable reciprocating member. The cassette 34 can include a magnetic disk 92 secured to one of the flexible side walls of a pumping chamber 68. The reciprocating member of the pump 90 is magnetically secured to the disk 92. Fluid is drawn into the chamber 68 when the reciprocating member or arm of the pump 90 retracts so as to expand the chamber 68. Fluid is pumped out of the chamber 68 when the reciprocating member or arm of the pump 90 extends and applies pressure to the pumping chamber 68 so as to compress the chamber. Since the volume of the pumping chamber 68 and the stroke of the reciprocating member or arm of the pump 90 are known, a known volume of fluid is pumped each time the reciprocating member retracts and extends.

The infusion pump 30 further includes a plurality of actuatable valve members 100, 102, and 103 used for occluding and permitting fluid flow in passageways of the cassette 34. Operation of these valves in combination with pumping strokes of pump 90 allow fluid to be pumped from the fluid source 18 to the patient 12. Valves 100, 102, and 103 are retractable valve members operatively connected to valve actuators 106 and individually actuatable to occlude or permit fluid flow through its associated fluid passage.

The valve member 100 is operatively coupled to the flexible passage line 64 so as to permit fluid flow through the passage 64 or to occlude fluid flow through the passage 64. Valve member 102 is operatively connected to passage 70 to permit or occlude fluid flow through the passage 70. Valve member 103 is operatively connected to flexible passage 72 to permit or occlude fluid flow through the passage 72.

A flow clip 108 is operatively connected to a flow clip actuator 110. The flow clip 108 is an elongated V-shaped occluding device that can be slid in one direction to occlude fluid flow through the cassette 34 and in another position to permit fluid flow through the cassette 34. During pump operation, the clip is positioned to allow fluid flow through the cassette 34.

The infusion pump 30 is positioned on an adjustable support stand (not shown) so that the height of the longitudinal axis of the cassette 34 is substantially at the patient's heart level 22. This positions the pressure sensing chamber 66 and pressure sensing transducer 80 at the patient's heart level.

The controller 86 is operatively connected to the valve actuators 106, to the flow clip actuator 110, and to pump 90 for the control and operation of fluid flow through the cassette 34, i.e., control of fluid pumping from the fluid source 18 to the patient 12. The controller 86 is also connected to the pressure transducer 80, to the data input source 46, and to manual control switches 48 and is responsive thereto.

When it is desired to pump fluid from the source 16 to the patient 12, valve 103 is actuated to occlude fluid communication to the patient while valves 100, 102 are open. The actuator arm of the pump 90 then retracts to fill the chamber 68 with fluid. Once the chamber 68 is filled with fluid, at least valve 100 is closed and valve 103 is opened. The pump 90 extends its actuator arm to compress the chamber 68 and pump fluid downstream toward and into the patient 12. During this compression of the chamber 68, valve 102 could also be closed.

When it is desired to monitor the peripheral venous pressure of the patient 12, the pump 90 is stopped and valve 100 actuated to occlude fluid communication between the fluid source 16 and the patient 12. Valves 102 and 103 are opened thereby forming a fluid column between the pressure sensing chamber 66 and the venous system of the patient 12. A predetermined time period, such as 15 seconds, is allowed to lapse or is timed out by controller 86. This time period is necessary to attenuate or remove the effects of pump actuation itself on any pressure measurements. After this time period lapses, the controller 86 monitors the output signal 82 of the pressure transducer 80. This pressure transducer signal is indicative of the peripheral venous pressure of the patient 12 and is also indicative of the mean systemic pressure of the patient.

The infusion pump 30 can be controlled open loop or closed loop. During surgery, it is contemplated that an open loop control would be used by the anesthesiologist to permit him maximum control of flow rate to control PVP. In nursing home or hospitalized settings or where large amounts of blood loss are not occurring, it is contemplated that a closed loop control would be preferred requiring less continuous monitoring by the health care providers.

Figure 3:
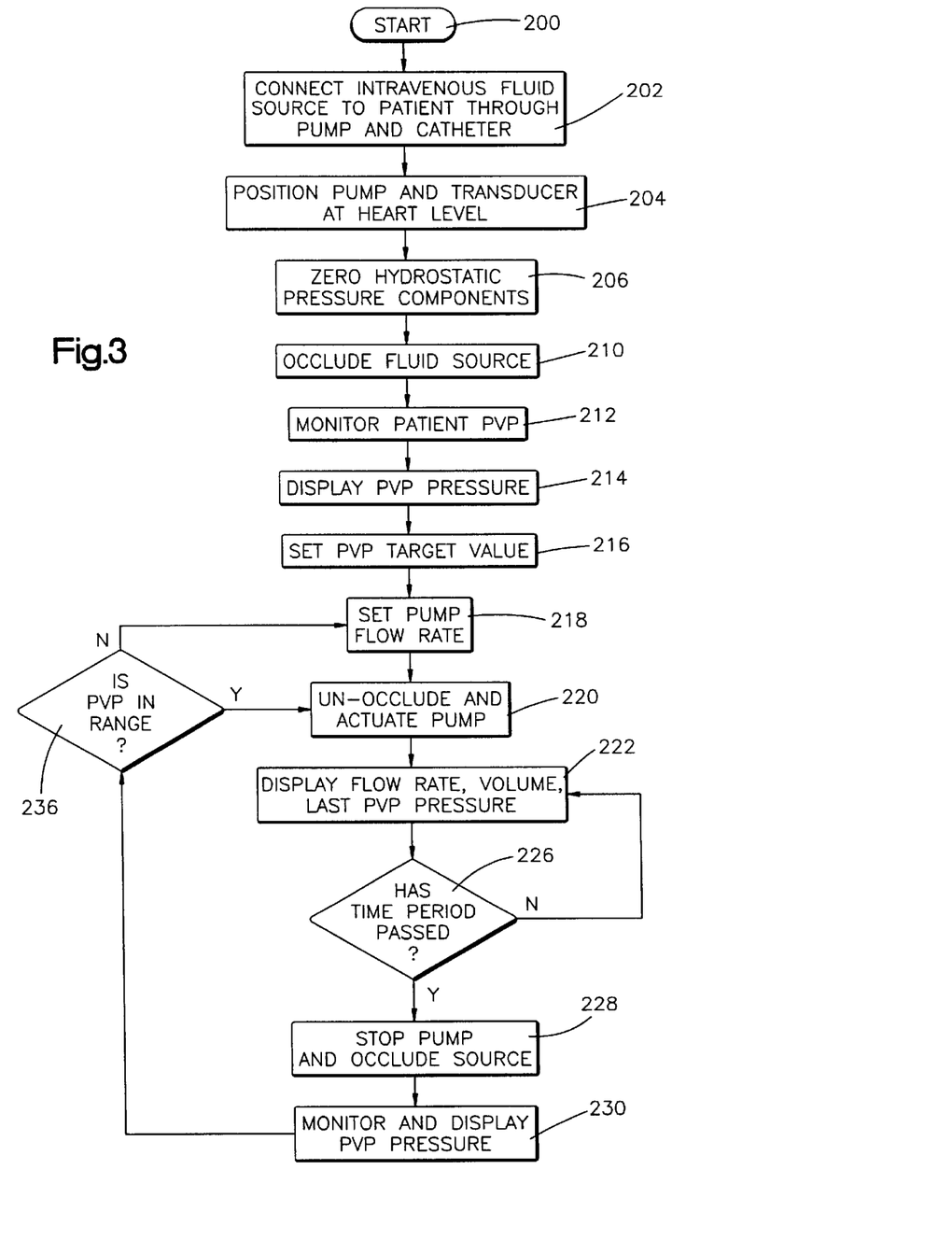
FIG. 3 is a flow diagram showing an open loop control process, in accordance with the present invention, for controlling fluid volume and hydration and for indicating resuscitation status of a patient.

Referring to FIG. 3, an open loop control process, in accordance with the present invention, for controlling blood volume and hydration and for indicating resuscitation status of the patient 12 is shown. In step 200, the infusion pump electronics are reset by clearing certain internal memories, setting initial flag conditions, etc. In step 202, an intravenous fluid source is connected to the patient through the infusion pump/cassette and catheter inserted into a peripheral vein. In step 204, the position of the pump and a pressure sensing transducer are adjusted so that the pump and the pressure sensing transducer device are located substantially at the heart level of the patient. The fluid source is occluded from the patient and an initial PVP measurement is made. The fluid source being occluded from the patient is accomplished by actuating valve 100. This occlusion is necessary to remove the pressure resulting from the fluid source per se from PVP measurements. The initial readings from the pressure transducer are hydrostatically zeroed in step 206 so that pressure measurements within the fluid line or conduit connected to the patient will indicate only venous pressure.

In step 210, fluid communication between the fluid source and the pressure measuring transducer is occluded (i.e., valve 100 is actuated to close off passage 64) and PVP is monitored in step 212. To determine an initial patient PVP value, several measurements or samples of the signal 82 from pressure transducer 80 may be made over time and an average value determined based upon a predetermined number of measurements. The patient's PVP value (as referred to herein, an averaged value) is then displayed in step 214.

In step 216, the clinician sets a target PVP value using the data input source 46 of the infusion pump based upon the initial value display in step 214. The set target value is preferably a target range. The infusion pump flow rate is set in step 218 at a value designed to maintain or achieve the set PVP target value in step 216. This flow rate can be entered through the data input source 46.

Three pump flow rates are preferably used in this control process. If the patient PVP pressure is within a range of its target value, a maintenance pump flow rate can be 70 cc/hr which is a value selected to hold or maintain the present PVP pressure within its present range assuming there is no substantial fluid loss. If it is decided that the patient's PVP rate needs to be increased, the pump flow rate selected to increase PVP can be 500 cc/hr. If it is determined that the patient's PVP value is greater than a target range and needs to be lowered, the pump flow rate selected to lower PVP can be 15 cc/hr. This low flow rate is known as the "keep-open" rate selected to keep the patient's vein/catheter interface open. The three different flow rates can be entered in through the data input source 46 and defined as the low, medium, and high flow rates. Flow rates other than these three can be used as well as additional flow rates can also be used in the control process.

In step 220, the fluid communication between the fluid source and the pump is unoccluded and the pump is actuated. In the pumping operation, the pump being in an unoccluded condition means that valves 100, 102, and 103 are periodically opened and closed in response to the operation of the pump 90 so as to pump fluid from the fluid source 16 to the patient 12. In step 222, the latest patient PVP measurement is displayed, the present fluid flow rate is displayed, and the total volume of fluid pumped to the patient is displayed. Also, the amount of remaining fluid in the fluid source can also be displayed.

In step 226, a determination is made as to whether a predetermined period of time has passed. This predetermined time is that time set by the clinician through the data input source 46 and is the amount of time desired between PVP measurements. If the determination in step 226 is negative, the process returns to step 222 where the flow rate, total volume of fluid pumped to the patient, and volume of fluid remaining in the fluid reservoir are updated and displayed. When the determination in step 226 is affirmative, the pump is stopped in step 228 and the fluid source is occluded from the patient fluid line or conduit, i.e., valve 100 is actuated to block or shut-off passage 64.

In step 230, the fluid pressure within the fluid pressure chamber 66 is monitored after a predetermined settling time has lapsed since pump shut-off, such as 15 sec. This time period permits settling of the venous system so as to remove effects of the pump 90 from pressure measurements. The new PVP measurement (newly determined average value) is then displayed on the display 50 for the clinician. A determination is then made in step 236 by the clinician as to whether the newly determined PVP value is within the range of the target value set in step 216. This range could be plus or minus 3 mmHg of a discrete set target value. Alternatively, the controller of the infusion pump can make this determination and then increase, decrease, or maintain pressure.

If the determination in step 236 is affirmative, the process returns to step 220 where the fluid source and pump are unoccluded (meaning that valve 100 is again permitted to open and close). The pump is again actuated and valves 100, 102, and 103 are periodically actuated and deactuated in synchronous with the pump 90 so as to pump fluid at a maintenance level. If the determination in step 236 is negative, a new pump flow rate is set in step 218 to either increase or decrease blood volume or hydration as required.

If step 236 determines the PVP is less than the target range, fluid flow needs to be increased. If step 230 determines the PVP is greater than the target range, fluid flow needs to be decreased. After the new flow rate is set in step 218, the pump is again actuated in step 220 and valves 100, 102, and 103 are actuated in such a manner as to pump fluid at a rate to either increase or decrease the blood volume or hydration of the patient.

At any time during the open loop control shown in FIG. 3, the clinician has the opportunity to adjust the operation of the pump, e.g., flow rate, using the manual control switches 48. The manual control switches allows the clinician to effectively override preset flow rates by increasing or decreasing the pump flow rate, force a new PVP value determination, or other desired control based upon his judgment.

Figure 4A:
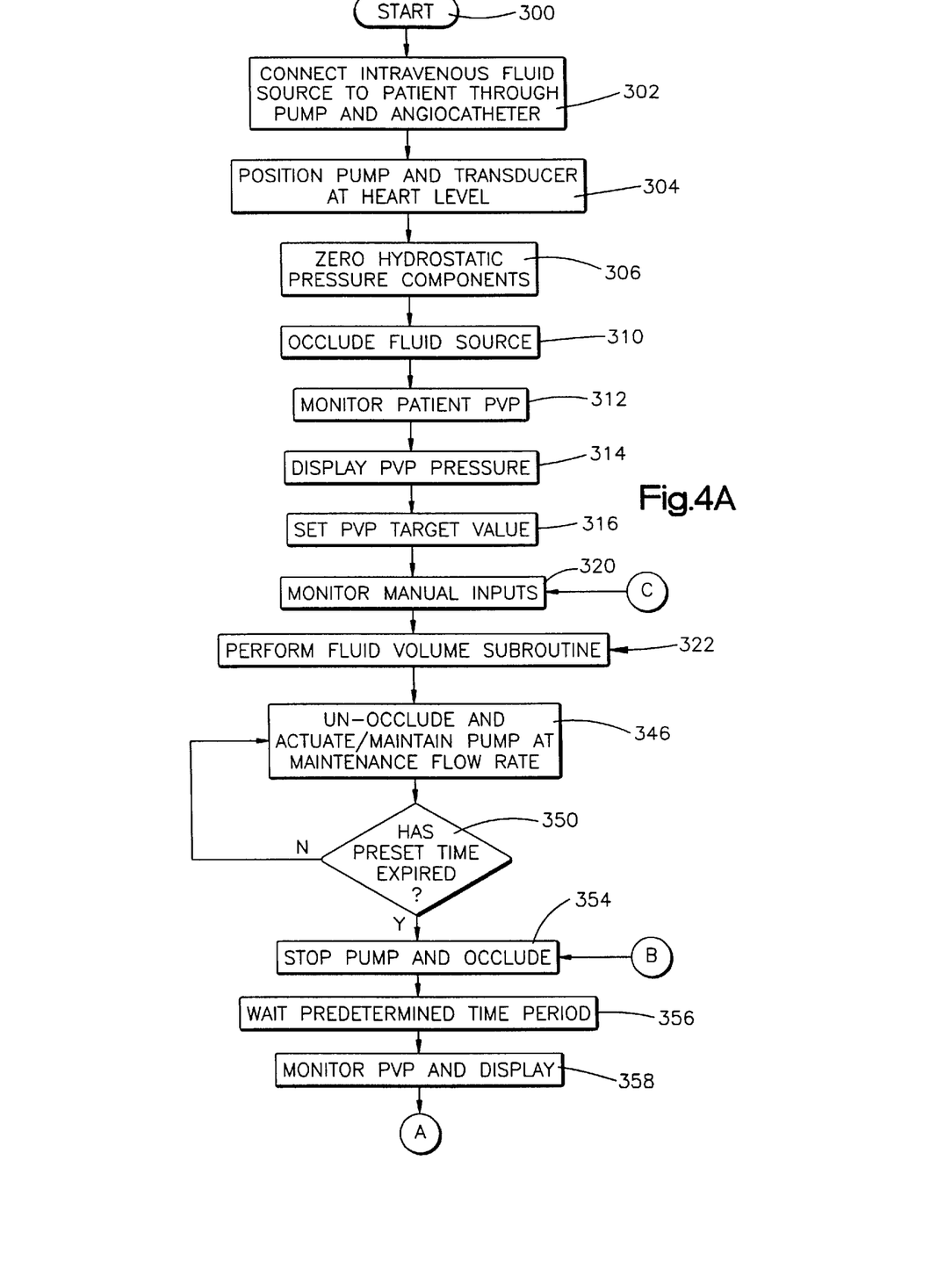
FIGS. 4A and 4B are flow diagrams showing a closed loop control process, in accordance with the present invention, for controlling fluid volume and hydration and for indicating resuscitation status of a patient.
Figure 4B:
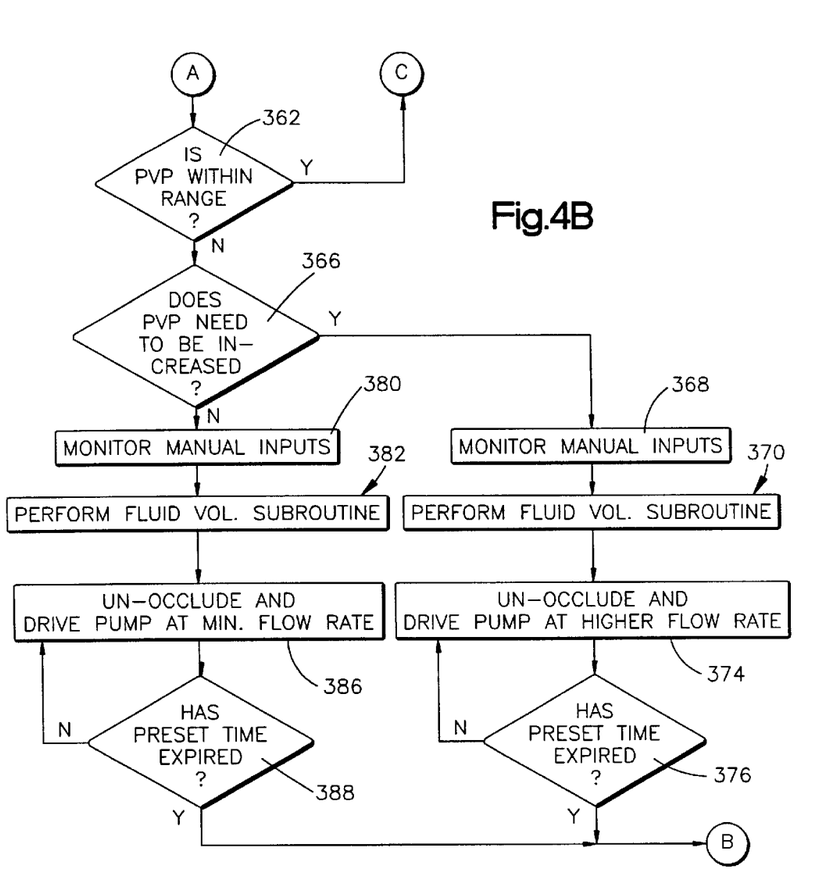

Referring to FIGS. 4A and 4B, a closed loop control process, in accordance with the present invention, for controlling blood volume and hydration and for indicating resuscitation status of a patient is depicted. This closed loop control is particularly useful in hospitalized or nursing home patients. In step 300, the infusion pump electronics are reset by clearing certain internal memories, setting initial flag conditions, etc. In step 302, an intravenous fluid source is connected to the patient through an infusion pump and catheter inserted in a peripheral vein. In step 304, the position of the pump and the pressure sensing transducer are adjusted so that the pump and the transducer measuring device are located substantially at the heart level of the patient. The fluid source is occluded from the patient and an initial PVP measurement is made. The fluid source being occluded from the patient is accomplished by actuating valve 100. This occlusion is necessary to remove the pressure from the fluid source per se from the PVP measurement. The initial pressure readings from the pressure transducer are hydrostatically zeroed in step 306 so that pressure measurements within the fluid line or conduit connected to the patient will indicate only venous pressure.

In step 310, fluid communication between the fluid source and the pressure measuring transducer is occluded (i.e., valve 100 is actuated to close-off passage 64) and a PVP measurement is monitored in step 312. To determine an initial patient PVP value, several measurements or samples of the signal 82 from pressure transducer 80 may be made over time and an average value determined based upon a predetermined number of measurements. The patient's PVP value (as referred to herein, an averaged value) is then displayed in step 314.

In step 316, the clinician sets a target PVP value using the data input source of the infusion pump based upon the initial value displayed in step 314. The set target value is preferably a target range. The infusion pump flow rate is set in step 318 at a value designed to maintain or achieve the set PVP target value in step 316.

Three pump flow rates are preferably used in this control process. If the patient PVP pressure is within a range of its target value, a maintenance pump flow rate can be 70 cc/hr which is a value selected to hold or maintain the present PVP pressure assuming there was no substantial fluid loss. If it is decided that the patient's PVP rate needs to be increased, the pump flow rate selected to increase PVP can be 500 cc/hr. If it is determined that the patient's PVP value is greater than a target value range and needs to be lowered, the pump flow rate selected to lower PVP can be 15 cc/hr. This low flow rate is the "keep-open" rate selected to keep the patient's vein/catheter interface open. The three different flow rates can be entered in through the data input source 46 and defined as the low, medium, and high flow rates. Flow rates other than these three can be used as well as additional flow rates can also be used in the control process.

Figure 5:
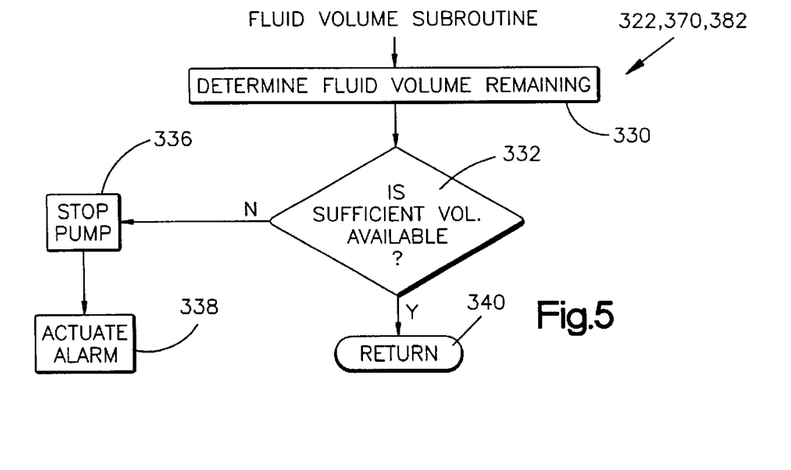
FIG. 5 is a flow diagram of a fluid volume subroutine used in the flow diagrams of FIGS. 4A and 4B.

In step 320, all of the manual inputs of manual control switches 48 are monitored. In step 322, a fluid volume subroutine is performed. Referring to FIG. 5, this subroutine is depicted. In step 330, a determination is made as to the remaining fluid volume remaining in the fluid source 16 such as IV 18. This volume is known since the initial volume of the source is known from a default value or from a value entered in through input source 46. A determination is made in step 332 as to whether or not there is a sufficient fluid volume available to continue (available to initiate the first time through the subroutine) operation of the infusion pump 30. If the determination is negative, the pump 30 is stopped or prevented from operation in step 336 and an alarm is activated in step 338. If the determination in step 332 is affirmative, the process returns in step 340 to the main control process.

Referring back again to FIGS. 4A and 4B, the infusion pump 30 is actuated or maintained at its maintenance flow rate in step 346. As described with regard to the open loop control arrangement, three pump levels may be used. A 70 cc/hr flow rate can be set to be a normal maintenance flow rate to maintain the patient's PVP level at its present state. A determination is made in step 350 as to whether a preset time period has expired. This time period is a time period entered through the data input 46 and is the time period between which PVP measurements are to be made. If the determination in step 350 is negative, meaning that the time period has not lapsed, the process returns to step 346 and the pump continues to pump. If the time period has expired, i.e., an affirmative determination in step 350, the pump is stopped and the fluid source 16 is occluded from the pump for the purpose of making a new PVP measurement (average value) in step 354 (i.e., valve 100 is actuated). A predetermined time period such as 15 sec. is allowed to lapse in step 356 to permit settling time within the fluid communication line and venous system of the patient so that a PVP measurement can be made. A PVP measurement or determination (based on an average of a plurality of samples) is made in step 358 after the time period in step 356. The new PVP measurement or determination (based on the averaged value) is displayed on the display 50.

A determination is then made in step 362 as to whether or not the PVP measured in step 358 is within the target value range such as plus or minus 3 mmHg from a particular value. If the determination is affirmative in step 362, the process returns to step 320. As part of the fluid value subroutine in step 322, it should be appreciated that the flow rate and the time between PVP measurements is considered in the determination as to whether there is sufficient fluid remaining in the source.

If the determination in step 362 is negative, the process proceeds to step 366 where a determination is made as to whether or not the PVP of the patient needs to be increased. If the determination in step 366 is affirmative, an indication of the need to increase PVP can be displayed and the process proceeds to step 368 where the manual input control switches 48 are again monitored to determine if a clinician desires an operational change. The fluid volume subroutine is performed again in step 370 to ensure that a sufficient fluid volume remains in the fluid source if pumped at a higher flow rate for the time period that will be allowed to lapse before a new PVP determination is made. Assuming a sufficient fluid volume does remain, the infusion pump 30 unoccludes the fluid source (valves 100, 102, and 103 are periodically opened and closed) and the pump is driven at a higher flow rate so as to pump at preferably 500 cc/hr in step 374. A determination is then made in step 376 as to whether a preset time period has expired. This time period is initially set through the data input source 46 and may be the same as or different as the preset time period in step 350. This time period is a time period desired between PVP measurements or determinations when the pump is driven at its higher flow rate. This time period is considered in the fluid volume subroutine 370. If the determination in step 376 is negative, the process returns to step 374. Once the determination in step 376 is affirmative, the process returns to step 354 where the process for determining a new PVP value is made.

If the determination in step 366 was negative, meaning that the patient's PVP needs to be decreased, the process proceeds to step 380 where the manual control switches 48 are monitored to determine if the clinician desires a change in operation. The process proceeds to step 382 where the fluid volume subroutine is performed taking into account the lower minimum pumping rate that will be used to decrease the patient's PVP and the time period that will be allowed to lapse between PVP measurements or determinations at the lower pump rate. Assuming a sufficient fluid volume supply remains taking into account the lower fluid flow rate and the time between PVP measurements, the fluid source is unoccluded (valves 100, 102, and 103 are periodically actuated) and the pump driven at the minimum flow rate in step 386. This lower fluid flow rate designed to lower the patient's PVP may be, for example, 15 cc/hr.

A determination is then made in step 388 as to whether a preset time period has expired. The preset time period used in step 388 is preset using the data input source 46 of the pump 30. This time period may be the same as that used in step 350 or 370 or may be different. This time period reflects the amount of time desired between determinations of PVP when the pump is driven at a lower flow rate.

If the determination in step 388 is negative, the process returns to step 386. If the determination in step 388 is affirmative, the process returns to step 354 where the process to monitor the next PVP value is performed.

After the pump is driven at either a higher rate to increase PVP or a lower rate to lower PVP, the program determines if the PVP has come back within the target range in step 362. Once the PVP has come back within range, the process returns to step 320 and pump flow rate is returned to the maintenance value in step 346.

The infusion pump 30 could include an additional pressure sensor (not shown) operatively connected to the fluid conduit that monitors for a pressure indicative of a continuous line occlusion during pumping resulting in a high pressure in the fluid conduit. This line occlusion sensor would be a higher pressure rated transducer than the PVP transducer 80. The line occlusion sensor would be connected to the controller 86. If the controller determines a continuous line occlusion exists during pumping, the pump would be stopped and an alarm sounded.

The present invention permits control of blood volume and hydration, and indicating resuscitation status by measuring PVP at a peripheral catheter/vein site. The present invention permits the delivery of fluid through a catheter while measuring PVP in the same fluid line or conduit. The PVP value determined in accordance with the present invention is indicative of the patient's mean systemic pressure.

From the above description of the invention, those skilled in the art will perceive improvements, changes and modifications. For example, flow rates can be different from those described. Also, a different type of infusion pump and in-line pressure sensing arrangement can be used. Preferably, the pressure sensor is in sensing communication with the fluid conduit at heart level and pressure measurements are made with the fluid source occluded and a predetermined time after the pump is shut-off. The PVP can be measured apart from the pump and the determined PVP value used to control the infusion pump. Such improvements, changes and modifications within the skill of the art are intended to be covered by the appended claims.

Having described the invention, the following is claimed:

1. An apparatus for measuring mean systemic pressure in a patient, comprising:
   a fluid source;
   a fluid conduit for carrying fluid from said fluid source to the patient;
   a pump for pumping fluid from said fluid source into the patient through said fluid conduit;
   a pressure sensing transducer coupled with said fluid conduit for measuring fluid pressure in said fluid conduit and providing a measured fluid pressure signal indicative thereof; and
   control means for controlling said pump and for controlling fluid communication through said fluid conduit so that the measured fluid pressure signal provided by said pressure sensing transducer is indicative of the mean systemic pressure of the patient.

2. The apparatus of claim 1 wherein said control means for controlling said pump controls said pump in response to the measured fluid pressure signal indicative of the mean systemic pressure of the patient so as to maintain the mean systemic pressure of the patient within a target range.

3. The apparatus of claim 2 wherein said control means includes an open loop controller.

4. The apparatus of claim 2 wherein said control means includes a closed loop controller.

5. An apparatus for measuring peripheral venous pressure in a patient, comprising:
   a fluid source;
   a fluid conduit for carrying fluid from said fluid source to the patient;
   a pump for pumping fluid from said fluid source into the patient through said fluid conduit; and
   a pressure sensing transducer coupled with said fluid conduit for measuring fluid pressure in said fluid conduit and providing a measured fluid pressure signal indicative thereof; and
   control means for controlling said pump and for controlling fluid communication through said fluid conduit so that the measured fluid pressure signal provided by said pressure sensing transducer is indicative of the peripheral venous pressure of the patient.

6. The apparatus of claim 5 wherein said control means for controlling said pump controls said pump in response to the measured fluid pressure signal indicative of the peripheral venous pressure of the patient so as to maintain the peripheral venous pressure of the patient within a target range.

7. The apparatus of claim 6 wherein said control means includes an occluder for occluding said fluid conduit to isolate said fluid source from the patient when said pressure sensing transducer measures fluid pressure in said fluid conduit indicative of the peripheral venous pressure of the patient.

8. The apparatus of claim 6 wherein said control means includes an open loop controller.

9. The apparatus of claim 6 wherein said control means includes a closed loop controller.

10. The apparatus of claim 6 wherein said control means controls said pump to one of three flow rates.

11. The apparatus of claim 10 wherein said control means controls said pump flow rate in response to the measured peripheral venous pressure so as to have a low flow rate to lower the peripheral venous pressure of the patient, a maintenance flow rate to maintain the peripheral venous pressure of the patient at a present pressure, and a high flow rate to increase the peripheral venous pressure of the patient.

12. An apparatus comprising:
    a fluid source;
    an electrically controlled pump for pumping fluid from said fluid source through a fluid conduit into a patient;
    a pressure sensing transducer for measuring a mean systemic pressure of the patient and providing a means systemic pressure signal indicative thereof; and
    control means for automatically controlling said pump in response to said means systemic pressure signal indicative of the measured mean systemic pressure of the patient.

13. The apparatus of claim 12 wherein said control means for controlling said pump includes an open loop controller.

14. The apparatus of claim 12 wherein said control means for controlling said pump includes a closed loop controller.

15. The apparatus of claim 12 wherein said pressure sensing transducer measures pressure in a peripheral vein of the patient.

16. An apparatus comprising:
    a fluid source;
    an electrically controlled pump for pumping fluid from said fluid source through a fluid conduit to a patient;
    a pressure sensing transducer for measuring peripheral venous pressure of the patient and providing a peripheral venous pressure signal indicative thereof; and
    control means for automatically controlling said pump in response to said peripheral venous pressure signal indicative of the measured peripheral venous pressure of the patient.

17. The apparatus of claim 16 wherein said control means for controlling said pump includes an open loop controller.

18. The apparatus of claim 16 wherein said control means for controlling said pump includes a closed loop controller.

19. An apparatus for controlling fluid volume in a patient comprising:
    a fluid source;
    a fluid conduit for carrying fluid from said fluid source to the patient;
    a controllable infusion pump for pumping fluid from said fluid source to a peripheral vein of the patient through said fluid conduit;
    controllable occluder for, when actuated, blocking fluid communication between said fluid source and the patient through said fluid conduit;
    fluid pressure sensor for sensing fluid pressure in said fluid conduit; and
    controller for controlling operation of said infusion pump and said occluder and for determining a peripheral venous pressure value from said sensed fluid pressure in said fluid conduit after said infusion pump is stopped by said controller and said controller actuates said occluder to block said fluid communication between said fluid source and the patient through said fluid conduit, said peripheral venous pressure being indicative of fluid volume of the patient.

20. The apparatus of claim 19 wherein said fluid conduit includes a disposable cassette having a pumping chamber and a pressure sensing chamber, said cassette being mountable within said infusion pump, said pressure sensor operatively coupled to said pressure sensing chamber and said occluder being located between said fluid source and said pressure sensing chamber.

21. The apparatus of claim 19 wherein said controller includes timing means for timing out a predetermined time period after said infusion pump is stopped, said controller determining said peripheral venous pressure based on sensed fluid pressure in said fluid conduit after said time period.

22. The apparatus of claim 19 wherein said controller includes means for determining said peripheral venous pressure value in response to averaging a plurality of said sensed pressure measurements in said fluid conduit and means for displaying said peripheral venous pressure.

23. An apparatus for controlling fluid volume in a patient comprising:
a fluid source;
a controllable infusion pump connected to said fluid source through a fluid inlet line;
a catheter inserted in a peripheral vein of a patient and connected to an outlet of said infusion pump through a fluid outlet line so as to provide a fluid communication path between the peripheral vein of the patient and said pump, activation of said pump resulting in fluid being delivered to the patient from said fluid source through said catheter;
an in-line pressure sensing transducer positioned substantially at a heart level of the patient for sensing pressure in the fluid communication path and providing a pressure measurement signal indicative thereof;
an actuatable in-line occluder for isolating said fluid source from the patient when the occluder is actuated;
control means for periodically stopping said infusion pump, actuating said occluder, monitoring said pressure measurement signal, and determining a peripheral venous pressure value of the patient in response thereto; and
means for adjusting operation of said infusion pump in response to the determined peripheral venous pressure value.

24. The apparatus of claim 23 further including a disposable cassette having a pumping chamber and a pressure sensing chamber, said cassette being mountable within said infusion pump, said pressure sensing transducer being operatively coupled to said pressure sensing chamber and said occluder being located between said fluid source and said pressure sensing chamber.

25. The apparatus of claim 23 wherein said control means includes timing means for timing out a predetermined time period after said pump is stopped, said peripheral venous pressure being determined after said time period.

26. The apparatus of claim 23 wherein said control means determines said peripheral venous pressure in response to an averaging of a plurality of said pressure measurement signal, said apparatus further including means for displaying said peripheral venous pressure.

27. A method for measuring mean systemic pressure in a patient, comprising the steps of:
connecting a fluid source to the patient through a fluid conduit;
pumping fluid from the fluid source into the patient through the fluid conduit; and
measuring fluid pressure using a pressure sensing transducer coupled to the fluid conduit by controlling the pumping and the flow of fluid from the fluid source to the patient so that the measured pressure with the pressure sensing transducer is indicative of the mean systemic pressure of the patient.

28. The method of claim 27 further including the step of controlling said pumping of fluid in response to the measured fluid pressure to maintain the mean systemic pressure of the patient within a target range.

29. The method of claim 28 wherein the step of controlling is open loop.

30. The method of claim 28 wherein the step of controlling is closed loop.

31. A method for measuring peripheral venous pressure in a patient, comprising the steps of:
connecting a fluid source to the patient through a fluid conduit;
pumping fluid from the fluid source into the patient through the fluid conduit; and
measuring fluid pressure using a pressure sensing transducer coupled to the fluid conduit by controlling the pumping and the flow of fluid from the fluid source to the patient so that the measured fluid pressure with the pressure sensing transducer is indicative of the peripheral venous pressure of the patient.

32. The method of claim 31 wherein the step of controlling fluid flow further includes the step of occluding the fluid conduit to prevent fluid flow from the fluid source to the patient before the step of measuring fluid pressure with the pressure sensing transducer indicative of the peripheral venous pressure of the patient.

33. The method of claim 31 wherein the step of controlling pumping further includes the step of controlling pumping of fluid in response to the peripheral venous pressure of the patient so as to maintain the peripheral venous pressure of the patient within a target range.

34. The method of claim 33 wherein said step of controlling pumping is open loop.

35. The method of claim 33 wherein said step of controlling pumping is closed loop.

36. The method of claim 33 wherein said step of controlling pumping includes controlling pumping to provide one of three possible flow rates.

37. The method of claim 31 wherein the step of controlling pumping further includes the step of controlling the pumping of fluid so as to pump at a low flow rate when the peripheral venous pressure of the patient needs lowered, at a maintenance flow rate when the peripheral venous pressure of the patient is to be maintained at a present pressure, and at a high flow rate when the peripheral venous pressure of the patient needs to be increased.

38. A method for controlling fluid volume in a patient comprising the steps of:
connecting a fluid source to the patient through a fluid conduit;
periodically pumping fluid with an infusion pump from the fluid source to a vein of the patient through the fluid conduit;
periodically occluding fluid communication between the fluid source and the patient through the fluid conduit;
periodically sensing fluid pressure in the fluid conduit with a pressure sensing transducer;
monitoring the sensed fluid pressure in the fluid conduit after the step of pumping stops, and the step of occluding blocks the fluid communication between the fluid source and the patient through the fluid conduit;

providing an electronic signal indicative of the monitored fluid pressure, the monitored fluid pressure being indicative of fluid volume of the patient; and controlling said pumping step in response to the electronic signal indicative of the monitored fluid pressure so as to control the fluid volume in the patient.

39. The method of claim 38 further including the step of timing out a predetermined time period after stopping of said pump, said step of monitoring the sensed fluid pressure in said fluid conduit occurring after said time period.

40. The apparatus of claim 38 wherein said step of monitoring includes determining an average of said pressure measurement signals and said method further includes the step of displaying said electronic signal indicative of the fluid volume.

41. A method comprising the steps of:

pumping fluid from a fluid source into a patient;

measuring a value functionally related to mean systemic pressure of the patient; and controlling said pumping in response to said measured value functionally related to mean systemic pressure of the patient.

42. A method comprising the steps of:

pumping fluid from a fluid source to a patient;

measuring peripheral venous pressure of the patient; and controlling said pumping in response to said measured peripheral venous pressure of the patient.

\* \* \* \* \*